US010416865B2

United States Patent
King et al.

(10) Patent No.: US 10,416,865 B2
(45) Date of Patent: Sep. 17, 2019

(54) MEDICAL DEVICE WITH ENHANCED USER INTERFACE CONTROLS

(71) Applicant: Welch Allyn, Inc., Skaneateles Falls, NY (US)

(72) Inventors: Catherine M. King, Ithaca, NY (US); Thomas A. Myers, Syracuse, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 301 days.

(21) Appl. No.: 15/194,275

(22) Filed: Jun. 27, 2016

(65) Prior Publication Data

US 2017/0336953 A1    Nov. 23, 2017

Related U.S. Application Data

(60) Provisional application No. 62/338,621, filed on May 19, 2016.

(51) Int. Cl.
*G06F 3/0484* (2013.01)
*G06F 3/0482* (2013.01)
(Continued)

(52) U.S. Cl.
CPC .......... *G06F 3/04847* (2013.01); *A61B 5/742* (2013.01); *G06F 3/0482* (2013.01);
(Continued)

(58) Field of Classification Search
CPC ........... H04N 1/00413; H04N 1/00424; H04N 1/00435; G06F 3/1253; G06F 3/04847;
(Continued)

(56) References Cited

U.S. PATENT DOCUMENTS 4,989,610 A * 2/1991 Patton ............... A61B 5/04365
600/508
5,614,993 A * 3/1997 Smith ............... G03G 15/5016
345/173

(Continued)

OTHER PUBLICATIONS

European Search Report for Application No. 17169480.5 dated Oct. 4, 2017.

*Primary Examiner* — Ryan F Pitaro
(74) *Attorney, Agent, or Firm* — Merchant & Gould P.C.

(57) ABSTRACT

A patient monitoring interface of a medical device includes a modifier screen including parameter selection regions having a predetermined size. At least one of the plurality of parameter selection regions includes parameter setting option subregions. A total set of parameter setting options includes a default subset of parameter setting options and a secondary subset of parameter setting options. In a primary display mode, the parameter selection region displays the default subset of parameter setting options in the predetermined number of parameter setting option subregions and an indicator region, with the secondary subset of parameter setting options not displayed. The indicator region is selectable to cause display of one or more of the secondary subset of parameter setting options in one or more of the parameter setting option subregions in place of a corresponding one or more of the default subset of parameter setting options.

1 Claim, 10 Drawing Sheets (51) Int. Cl.
  *A61B 5/00* (2006.01)
  *G16H 40/63* (2018.01)
  *A61B 5/01* (2006.01)
  *A61B 5/021* (2006.01)
  *A61B 5/024* (2006.01)
  *A61B 5/08* (2006.01)
  *A61B 5/145* (2006.01)

(52) U.S. Cl.
  CPC ......... *G06F 3/04842* (2013.01); *G16H 40/63* (2018.01); *A61B 5/01* (2013.01); *A61B 5/021* (2013.01); *A61B 5/024* (2013.01); *A61B 5/0816* (2013.01); *A61B 5/14542* (2013.01); *A61B 2560/0437* (2013.01)

(58) Field of Classification Search
  CPC ... G06F 3/0482; G06F 3/04842; G16H 40/63; A61B 5/742
  See application file for complete search history.

(56) References Cited

U.S. PATENT DOCUMENTS

| | | | | |
|---|---|---|---|---|
| 5,880,727 | A * | 3/1999 | Barrett | H04N 1/00408 399/81 |
| 6,037,939 | A * | 3/2000 | Kashiwagi | G06F 3/038 715/767 |
| 6,188,407 | B1 * | 2/2001 | Smith | A61B 5/044 715/841 |
| 6,239,880 | B1 * | 5/2001 | Barrett | H04N 1/00352 347/129 |
| 6,353,899 | B1 * | 3/2002 | Martin | G03G 15/55 714/47.2 |
| 6,470,155 | B1 * | 10/2002 | Martin | G06F 3/04847 399/81 |
| 6,590,586 | B1 * | 7/2003 | Swenton-Wall | G06F 17/30274 707/E17.029 |
| 6,915,299 | B1 * | 7/2005 | Arcuri | G06F 17/30011 |
| 8,677,267 | B2 * | 3/2014 | Litwiller | G06F 17/241 399/367 |
| 9,922,018 | B2 * | 3/2018 | Chan | G06F 17/246 |
| 2001/0026290 | A1 * | 10/2001 | Machida | H04N 1/00411 715/810 |
| 2003/0135087 | A1 * | 7/2003 | Hickle | G06F 19/3456 600/26 |
| 2006/0013610 | A1 * | 1/2006 | Martin | G03G 15/5016 399/81 |
| 2006/0049936 | A1 * | 3/2006 | Collins, Jr. | A61B 5/1115 340/539.11 |
| 2007/0115267 | A1 * | 5/2007 | Motoyoshi | H04N 1/00411 345/173 |
| 2007/0138069 | A1 * | 6/2007 | Roncadi | A61M 1/16 210/96.2 |
| 2008/0103533 | A1 * | 5/2008 | Patel | A61N 1/36082 607/2 |
| 2008/0104514 | A1 * | 5/2008 | Kang | G11B 27/34 715/719 |
| 2008/0229212 | A1 * | 9/2008 | Miyazaki | G06F 9/44505 715/744 |
| 2008/0281168 | A1 * | 11/2008 | Gibson | A61B 5/0205 600/301 |
| 2009/0064050 | A1 * | 3/2009 | Aono | H04N 1/00411 715/843 |
| 2010/0169376 | A1 * | 7/2010 | Chu | G06F 17/30973 707/780 |
| 2010/0235782 | A1 * | 9/2010 | Powell | G06F 19/3418 715/809 |
| 2011/0004071 | A1 * | 1/2011 | Faiola | A61B 5/7445 600/300 |
| 2011/0035671 | A1 * | 2/2011 | Iwai | H04N 1/00347 715/728 |
| 2011/0140896 | A1 * | 6/2011 | Menzel | A61B 5/02055 340/573.1 |
| 2011/0271222 | A1 * | 11/2011 | Cho | G06F 3/0481 715/773 |
| 2011/0317196 | A1 * | 12/2011 | Yasuda | G06F 3/1205 358/1.13 |
| 2012/0002232 | A1 * | 1/2012 | Inui | H04N 1/00 358/1.13 |
| 2012/0197728 | A1 * | 8/2012 | Luna | G06Q 30/02 705/14.64 |
| 2013/0007809 | A1 * | 1/2013 | Hays | H04N 21/4131 725/47 |
| 2013/0061174 | A1 * | 3/2013 | Buchanan | G06Q 30/0601 715/810 |
| 2013/0080885 | A1 * | 3/2013 | Boyd | G06F 17/243 715/255 |
| 2013/0117704 | A1 * | 5/2013 | Lahoutifard | G06F 3/04815 715/780 |
| 2013/0167089 | A1 * | 6/2013 | Abe | G06F 3/04817 715/835 |
| 2013/0172710 | A1 * | 7/2013 | Mears | G06F 19/3468 600/365 |
| 2013/0190717 | A1 * | 7/2013 | Dollar | A61M 5/172 604/505 |
| 2013/0201222 | A1 * | 8/2013 | Doyle | G16H 40/63 345/672 |
| 2013/0226352 | A1 * | 8/2013 | Dean-Hendricks | F24F 11/30 700/276 |
| 2013/0263058 | A1 * | 10/2013 | Hoerentrup | G06F 3/048 715/840 |
| 2013/0267793 | A1 * | 10/2013 | Meador | A61B 5/0205 600/301 |
| 2013/0283197 | A1 * | 10/2013 | Skidmore | A61M 16/0051 715/771 |
| 2014/0136939 | A1 * | 5/2014 | Chan | G06F 17/246 715/227 |
| 2014/0143736 | A1 * | 5/2014 | Huang | G06Q 10/0637 715/854 |
| 2014/0281967 | A1 * | 9/2014 | Bodnick | G06Q 10/10 715/708 |
| 2015/0063907 | A1 * | 3/2015 | Graham | E01C 23/07 404/84.1 |
| 2015/0092228 | A1 * | 4/2015 | Okabayashi | G03G 15/502 358/1.15 |
| 2015/0145793 | A1 * | 5/2015 | Shimizu | G06F 3/0488 345/173 |
| 2015/0212989 | A1 * | 7/2015 | Rice | G06F 17/2247 715/234 |
| 2015/0248534 | A1 * | 9/2015 | Krzywicki | G06F 19/3406 715/771 |
| 2015/0301717 | A1 * | 10/2015 | Wekell | G16H 15/00 715/835 |
| 2015/0350639 | A1 * | 12/2015 | Maule | G06F 3/0481 348/187 |
| 2016/0026371 | A1 * | 1/2016 | Lu | G06F 3/04845 715/765 |
| 2016/0080465 | A1 * | 3/2016 | Sasaki | H04L 67/025 715/740 |
| 2016/0094737 | A1 * | 3/2016 | Sugiura | H04N 1/00432 358/1.15 |
| 2016/0128646 | A1 | 5/2016 | King et al. | |
| 2016/0154548 | A1 * | 6/2016 | Kajiyama | G03B 17/14 715/825 |
| 2016/0291812 | A1 * | 10/2016 | Ogura | G06F 3/0482 |
| 2017/0315687 | A1 * | 11/2017 | Yoshida | G06F 3/0482 |
| 2018/0005195 | A1 * | 1/2018 | Jacobson | G06Q 10/1095 |
| 2018/0074684 | A1 * | 3/2018 | Sun | G06F 17/30539 |

* cited by examiner

MEDICAL DEVICE WITH ENHANCED USER INTERFACE CONTROLS

CROSS-REFERENCE TO RELATED APPLICATIONS

The present application claims priority from U.S. Provisional Patent Application No. 62/338,621, filed on May 19, 2016, the disclosure of which is hereby incorporated by reference in its entirety.

BACKGROUND

As the amount of information that is captured by medical devices increases, the complexity of using the devices also increases. This complexity extends into how the data is displayed to the user. In some interfaces, the amount of data that is provided can function to obscure important information, particularly when the display is viewed at a distance. In particular, specific monitored values and associated parameters and parameter settings may be difficult to display and/or select and may require a large number of selections to navigate to a particular parameter or parameter setting in a displayed menu due to the number of parameters requiring selection. Further, limited space for navigation features on a display may be provided.

SUMMARY

In a first aspect, a medical device includes a processor, a display, and a memory. The memory has encoded instructions stored thereon that, when executed by the processor, cause the processor to create a patient monitoring interface on the display. The patient monitoring interface includes a modifier screen including a plurality of parameter selection regions, each of the plurality of parameter selection regions having a predetermined size, wherein at least one of the plurality of parameter selection regions includes a predetermined number of parameter setting option subregions, the predetermined number of parameter setting option subregions being fewer than a total set of parameter setting options available. The total set of parameter setting options includes a default subset of parameter setting options and a secondary subset of parameter setting options. In a primary display mode, the parameter selection region displays the default subset of parameter setting options in the predetermined number of parameter setting option subregions and an indicator region, with the secondary subset of parameter setting options not displayed. The indicator region is selectable to cause display of one or more of the secondary subset of parameter setting options in one or more of the parameter setting option subregions in place of a corresponding one or more of the default subset of parameter setting options.

In a second aspect, a medical device includes a processor, a display, and a memory. The memory has encoded instructions stored thereon that, when executed by the processor, cause the processor to create a patient monitoring interface on the display. The patient monitoring interface includes a modifier screen including a plurality of parameter selection regions, each of the plurality of parameter selection regions included in a row aligned with a modifier of a patient measurement to be monitored and having a predetermined number of subregions associated with different parameters, and wherein the predetermined number of subregions is lower than a total number of parameters associated with the modifier. The modifier screen includes, for at least one of the plurality of parameter selection regions, a display of an initial parameter in each of the plurality of parameter selection subregions and display of an indicator region at an end of the row which, when selected, causes the plurality of parameter selection subregions to cycle through a set of parameters, the set of parameters including a number of parameters greater than the number of parameter selection subregions. The modifier screen further includes, for at least one of the plurality of parameter selection subregions, display of a plurality of parameter setting option subregions and a second indicator region, which, when selected, causes the plurality of parameter setting option subregions to cycle through a set of parameter settings, the set of parameter settings including a number of parameter settings greater than the number of parameter setting option subregions.

In a third aspect, a medical device includes a processor, a display, and a memory. The memory has encoded instructions stored thereon that, when executed by the processor, cause the processor to create a patient monitoring interface on the display. The patient monitoring interface includes a home screen displaying a plurality of monitored values in a corresponding plurality of home screen monitoring regions, and wherein one or more of the home screen monitoring regions includes a modifier display subregion displaying one or more selected modifiers including parameters and selected parameter options selected in the modifier screen. The patient monitoring interface further includes a modifier screen reached based on selection of the modifier display subregion and including a plurality of parameter selection regions, each of the plurality of parameter selection regions included in a row aligned with a modifier of a patient measurement to be monitored and having a predetermined number of subregions associated with different parameters, and wherein the predetermined number of subregions is lower than a total number of parameters associated with the modifier. The modifier screen further includes, for at least one of the plurality of parameter selection regions, display of an initial parameter in each of the plurality of parameter selection subregions and display of an indicator region at an end of the row which, when selected, causes the plurality of parameter selection subregions to cycle through a set of parameters, the set of parameters including a number of parameters greater than the number of parameter selection subregions. The modifier screen also includes, for at least one of the plurality of parameter selection subregions, display of a plurality of parameter setting option subregions and a second indicator region, which, when selected, causes the plurality of parameter setting option subregions to cycle through a set of parameter settings, the set of parameter settings including a number of parameter settings greater than the number of parameter setting option subregions. The processor is further configured to, in response to selection by a user of a confirmation button on the modifier screen, determine whether a required parameter setting option remains unselected, and, in response to determining that a required parameter setting option remains unselected, display a notification message on the display indicating to select the required parameter setting option.

DETAILED DESCRIPTION

Examples of ambulatory care environments can include hospitals, clinics, managed care facilities, and other locations where medical care is provided. Medical personnel in ambulatory care environments can utilize vital signs monitoring devices, vital signs displays, personal computing devices and electronic medical record access portals. Medical staff and providers often need to record a patient's vital signs and enter those vital signs into the patient's electronic medical record. Currently, providers must perform vital signs measurements, remember the measurements, and then enter those measurements into one or more computing devices which may or may not be directly linked to the patient's electronic medical record.

In the context of the present application, a device having vital sign monitoring features is disclosed that allows for selection, via a graphical user interface, of various options by selecting different regions, or subregions, of the display that display a particular parameter or option that can be selected for use in connection with monitoring an associated patient measurement (e.g., a vital sign) of a patient. The device as described herein allows for improved selection characteristics by improving the operational efficiency of a device, and requiring fewer keystrokes to navigate to a particular option or parameter for selection, particularly in view of the wide variety of different patient measurements monitored and possible parameters that can be set in association with each patient measurement.

Figure 1:
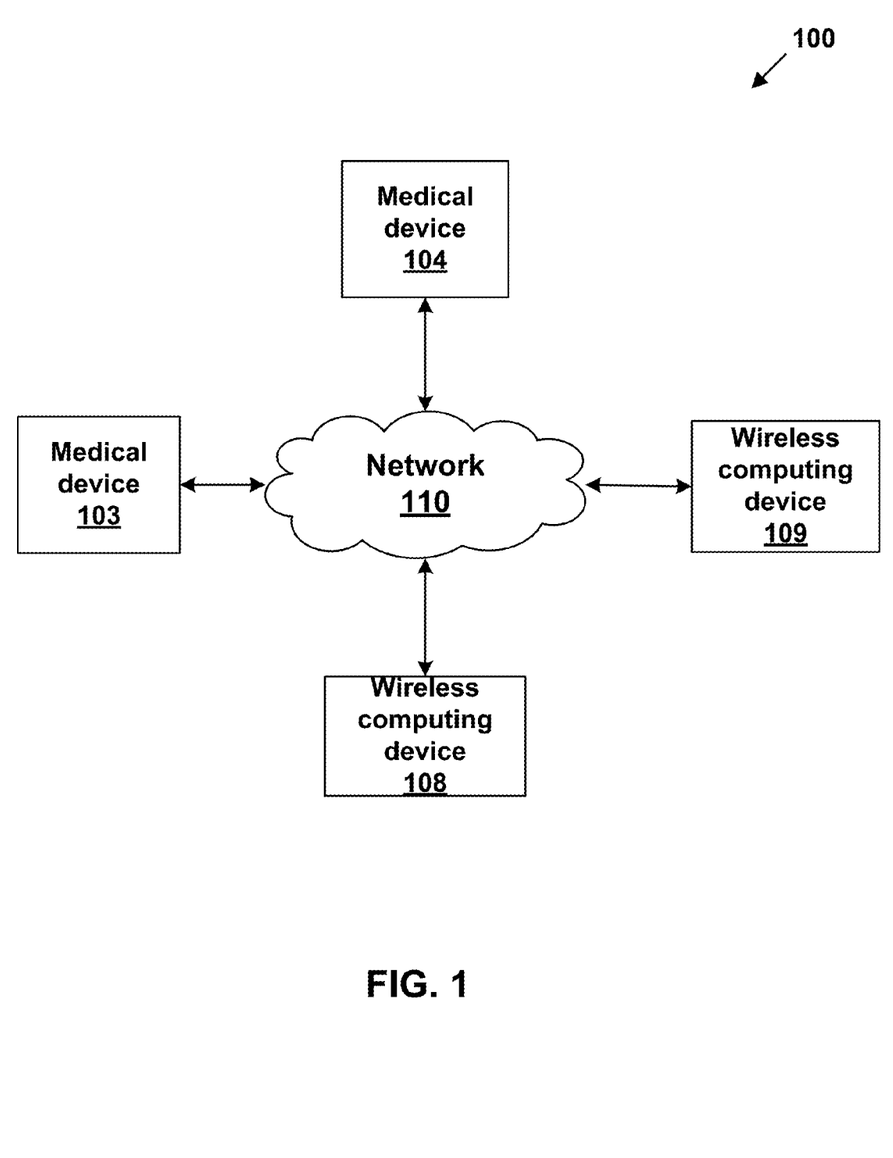
FIG. 1 illustrates a block diagram of a wireless ambulatory care system.

FIG. 1 illustrates a block diagram of an example wireless ambulatory care network 100. The example network 100 includes medical devices 103 and 104, wireless computing devices 108 and 109, and communication network 110. In embodiments, the example network 100 can include more or fewer medical devices 103 and 104. In embodiments, the example network can include more or fewer wireless computing devices 108 and 109. The communication network 110 can be a wireless network, such as WiFi, Bluetooth, Zigbee, Ant, Z-Wave, etc.

In some embodiments, the one or more medical devices 103 and 104 can include one or more vital signs measurement components. For example, the medical devices 103 can include, for example, a thermometer, a heart rate monitor, a pulse oximeter, a non-invasive blood pressure monitor, and a respiration rate monitor. In embodiments, one or more vital signs measurement components are wirelessly linked to the medical devices 103 and 104 and can transmit measurements to the medical devices 103 and 104.

Example computing components of medical devices 103 and 104 are shown and described in more detail with reference to FIG. 10, below.

In some embodiments, the one or more wireless computing devices 108 and 109 can be smart phones, tablet computers, personal digital assistants, laptop computers, and desktop computers, which can optionally be mounted on portable carts. Example computing components of the one or more wireless computing devices 108 and 109 are shown and described in more detail with reference to FIG. 10, below. The use of less complicated wireless computing devices 108 and 109, such as heart rate monitors, pulse oximeters, etc., is also contemplated by this document.

Figure 2:
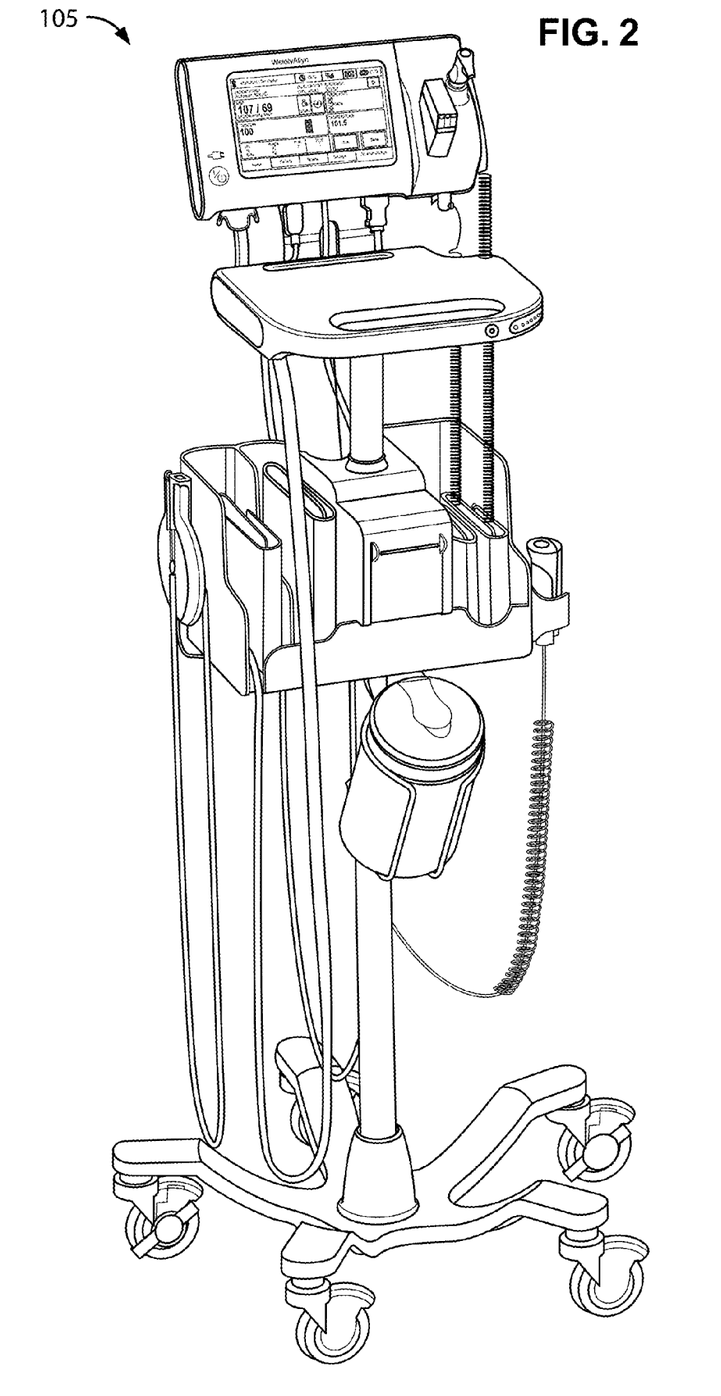
FIG. 2 illustrates an example medical device of the system of FIG. 1.
Figure 3:
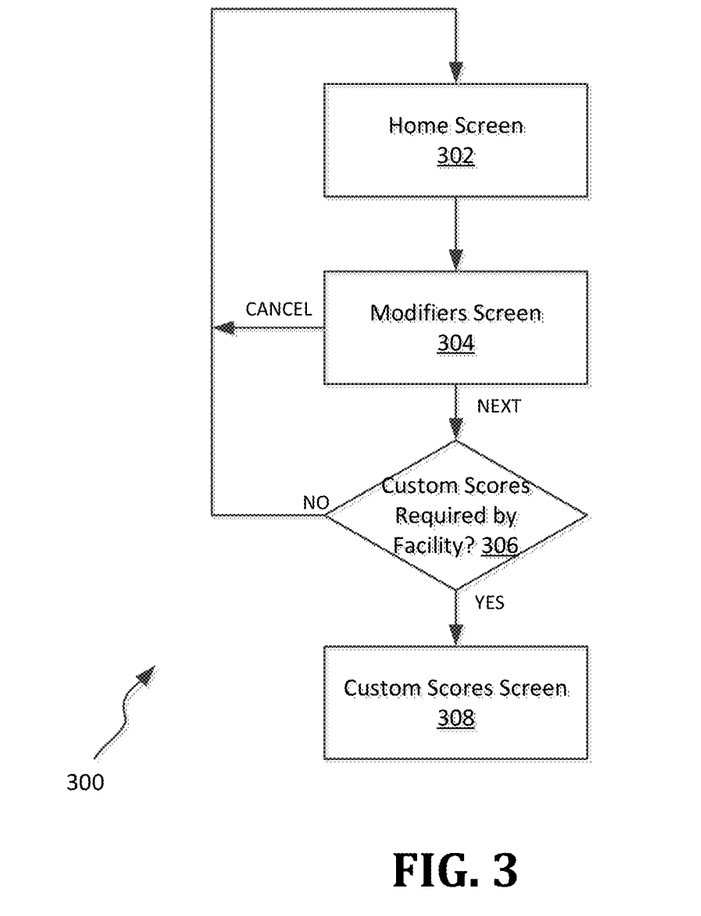
FIG. 3 illustrates a flowchart of example screen navigation sequences according to an example embodiment of the present disclosure.

FIG. 2 illustrates one example of the medical device 105. The medical device 105 is shown on a mobile cart, and the medical device 105 is programmed to provide the functionalities described herein. The medical device 105 includes a user interface, such as a touch screen, and includes the ability to execute multiple workflows or profiles. In some embodiments, the medical devices 105 and 106 in FIGS. 2 and 3 are the medical device 103 or 104 shown in, and described with reference to, FIG. 1. Other embodiments can include more or fewer components than those shown in FIG. 2, or include different components that accomplish the same or a similar function.

The medical device 105 is able to operate within one or more profiles. A profile is a series of one or more tasks that a user of the medical device 105 performs. When the medical device 105 operates within a profile, the medical device 105 provides functionality suitable for assisting the user in performing the profile. When the medical device 105 operates within different profiles, the medical device 105 provides different functionality.

When the medical device 105 is manufactured, the medical device 105 is configured to be able to operate within one or more profiles. After the medical device 105 is manufactured, the medical device 105 can be reconfigured to operate within one or more additional profiles. In this way, a user can adapt the medical device 105 for use in different profiles as needed.

In various embodiments, the medical device 105 operates within various profiles. For example, in some embodiments, the medical device 105 can operate within a monitoring profile or a non-monitoring profile. Example types of non-monitoring profiles include, but are not limited to, a spot check profile and an office profile. An example of a monitoring profile includes, but is not limited to, an intervals profile.

Figure 4:
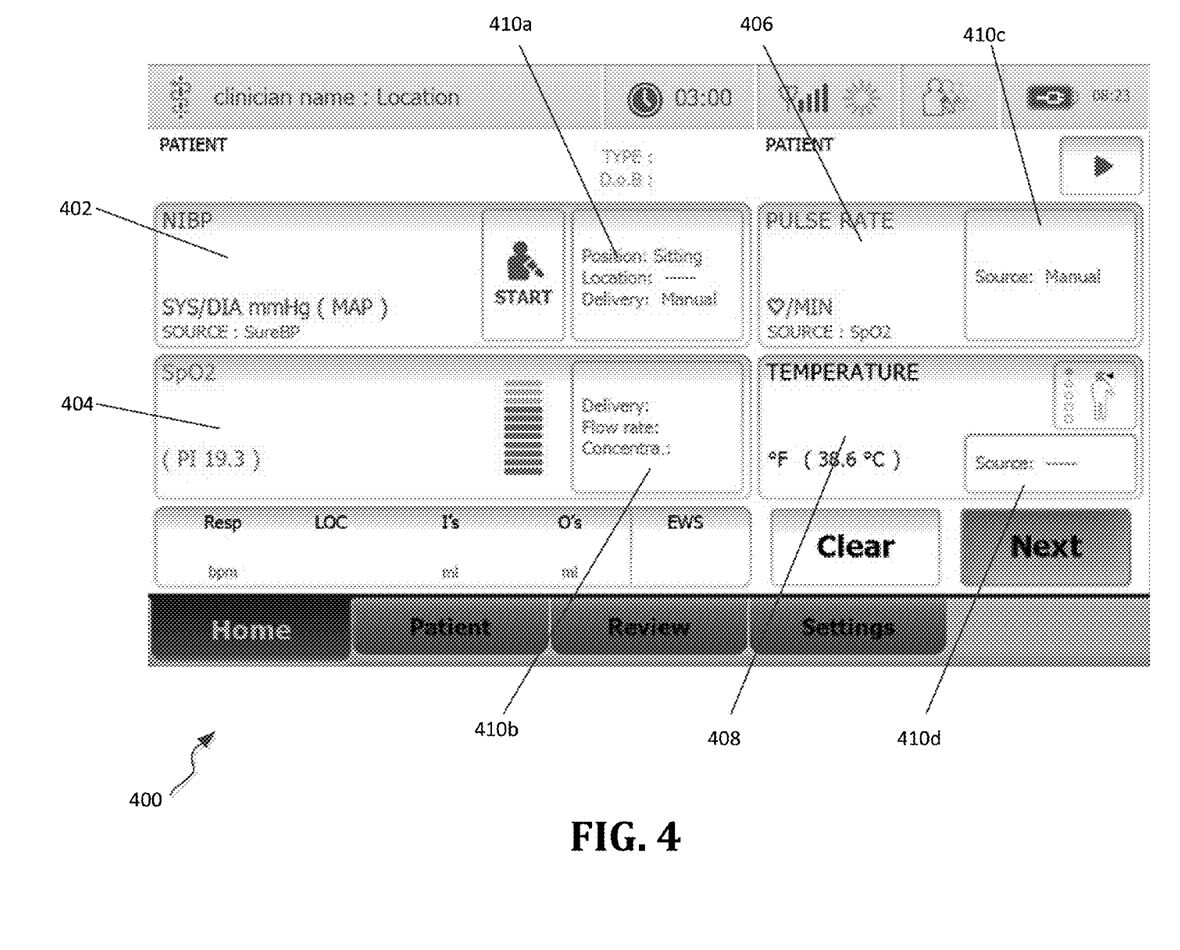
FIG. 4 illustrates an example home screen presented on a display of the medical device of FIG. 2.

FIG. 3 illustrates a flowchart of an example screen navigation sequence 300 according to an example embodiment of the present disclosure. In the embodiment shown, a home screen is displayed (step 302) by default during the screen navigation sequence 300. One example home screen 400 is discussed in further detail below in connection with FIG. 4. If a modifier region is selected on the home screen 400 (e.g., as seen in FIG. 4, above), a modifier screen is displayed (step 304) on a display of the medical device. An example of such a modifier screen is modifier screen 500 seen in FIG. 5, discussed below.

Figure 5:
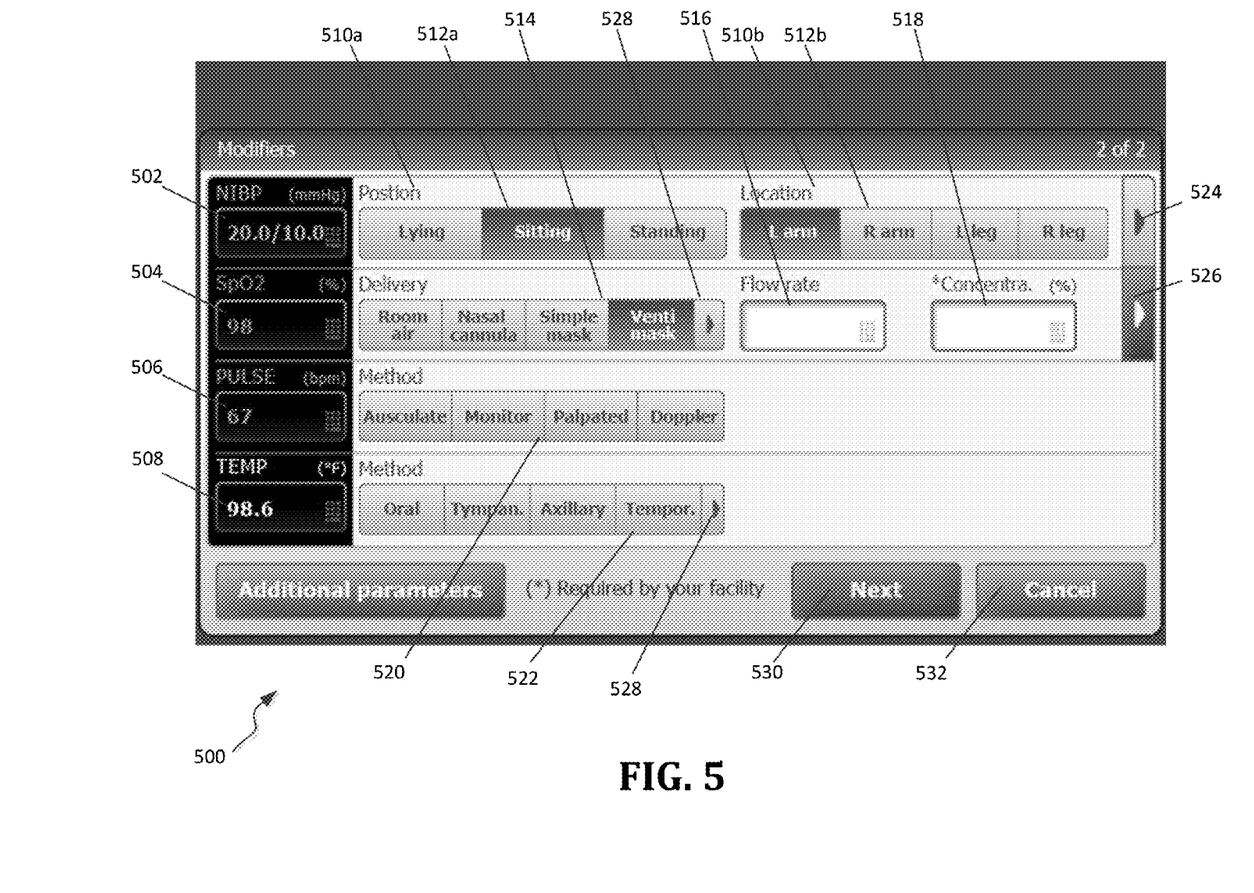
FIG. 5 illustrates an example modifier screen presented on a display of the medical device of FIG. 2.

A determination operation (step 306) is performed to determine a subsequent screen to be displayed based on a user selection on the modifier screen 500. If a "cancel"

option is selected on a modifier screen 500, the home screen 400 will be displayed (returning to step 302). However, if a "Next" option is selected on the modifiers screen (or some equivalent confirmation message, such as "OK", or "Accept", etc.) the medical device will determine whether any particular custom scores are required by a facility (step 308). If no custom scores are required, the medical device can return to the home screen 400 directly (step 304). However, if custom scores are required (e.g., additional scores used in monitoring), a custom scores screen may be displayed to further lead a user to select specific custom scores for a particular patient (step 308). Such custom scores are generally known in the art, and form no portion of the present disclosure. Upon selection of such scores, the medical device can return to the home screen 400.

Referring now to FIG. 4, an example home screen 400 presented on a display of the medical device of FIG. 2 is shown. The home screen 400 represents one possible example of a home screen useable in the screen navigation sequence 300 described above in connection with FIG. 3.

In the example shown, the home screen 400 includes a header region displaying a clinician name and location, connectivity, time, and other operating information, as well as patient identifying information such as a patient name. In addition to this operating information, monitored information is displayed. Such monitored information can include a plurality of regions 402-408 displaying monitored values. In the example shown, a NIBP region 402, a SpO2 region 404, a pulse rate region 406, and a temperature region 408 are shown; however, in other embodiments, other monitored values could be displayed as well.

Further, and relevant to the present disclosure, each of regions 402-408 include a modifier display region 410, shown as modifier display regions 410a-d positioned within each of regions 402-408, respectively. The modifier display regions 410a-d display one or more modifiers that are set for each monitored value, which may define, for example, additional details regarding a manner in which such monitored values are captured, a location of the data capture, specific delivery parameters, and sources of such information. Other modifiers may be included as well. In the embodiment shown, the modifier display regions 410a-d are user-selectable, for example via a touch-screen display. Selection of one of the modifier display regions 410a-d can result in display of a modifier screen 500, discussed in further detail below.

In addition to the regions 402-408 and modifier display regions 410a-d, one or more additional details may be provided on the home screen 400 as well. For example, patient details and/or settings may be set using the home screen, as well as details regarding other types of monitored values (e.g., respiration, location, etc.) can be assessed and displayed as well.

FIG. 5 illustrates an example modifier screen 500 presented on a display of the medical device of FIG. 2. The modifier screen 500 represents one possible example of a modifier screen useable in the screen navigation sequence 300 described above in connection with FIG. 3. In that context, the modifier screen 500 can be reached, either directly or indirectly, in response to selection of a modifier display region 410 of the home screen 400 of FIG. 4.

In the embodiment shown, the modifier screen includes a plurality of parameter selection regions 502, 504, 506, 508 which correspond to regions 402-408, respectively. Each of the parameter selection regions 502-508 are, in this embodiment, arranged in a row alignment, although other alignments (e.g., vertical) could be used as well. In this embodiment, each row, associated with a separate monitored value, allows modifiers to be defined by selecting parameters, and then selecting a parameter option or entering a parameter value, for such parameters. For example, in the NIBP region 502, parameters "Position" and "Location" are identified, with the "Position" parameter having possible option settings of "Lying", "Sitting", or "Standing", while in the "Location" parameter possible parameter options include "L arm", "R arm", "L leg", and "R Leg".

It is noted that both parameters 510a-b include parameter option setting regions 512a-b of predetermined size, in that each parameter has options displayed that extend approximately half a width of the screen (except for the modifier value positioned along a left edge of the screen). Each parameter selection region, shown as regions 512a-b, has a set of parameter settings displayed, shown in parameter setting option subregions, which are selectable by selecting a particular parameter setting option subregion.

In further examples, such as in association with the SpO2 modifier and parameter selection region 504, separate delivery, flow rate, and concentration parameters are included, and parameter setting option regions 514, 516, and 518 are displayed. In this example, parameter setting option region 514 includes a plurality of subregions that are aligned in a row, while parameter setting option regions 516, 518 are sized to receive a numerical value, for example which can be entered into a pop-up keypad which appears in response to selection of one of regions 516, 518, respectively. However, in general, each of regions 516, 518 is sized to reside in approximately one fourth of the row for parameter selection region 504. Similar regions exist for other parameter selection regions, with parameter setting option region 520 residing within parameter selection region 506 and defining a manner of pulse detection, and parameter setting option region 522 residing within parameter selection region 508, defining a type of temperature determination to be made.

Within the context of the present disclosure, for the instances in which a parameter selection region includes more parameters than there is room to display, an indicator may be included along a side of that parameter selection region which may assist in navigating to a display of additional parameters and associated parameter setting options. In the embodiment shown, parameter selection region 502 includes indicator 524, and parameter selection region 504 includes indicator 526. Because, in both regions 502, 504, parameters exceed the space presented, the indicator can be selected to display any additional parameters and parameter setting options associated with that parameter that may be available for selection. A user may select indicator 524 or indicator 526 to scroll one or more positions and cause display of those additional available parameters. In one example embodiment, due to the illustration of the indicator 524 oriented to the right, the parameters will rotate onto the screen, with a leftmost parameter (Position) disappearing, a rightmost parameter (Location) moving to the left, and a new (previously hidden) parameter, not shown, taking place of that rightmost parameter. Similarly, selection of indicator 526 may cause a Delivery parameter to disappear, would move the Flow rate and Concentration parameters to the left side of the screen within region 504, and cause at least one further parameter to be displayed. That further parameter would reside within a rightmost portion of the region 504, and/or may include two parameter setting option regions, if such regions are associated with parameters requiring numerical value inputs such as the Flow Rate and Concentration parameters.

In additional examples, indicators 524, 526 can cause rotation or shifting of parameters by more than one "position", for example by completely replacing a row of four parameters and associated parameter setting option regions with previously-hidden parameters and parameter setting option regions. In alternative embodiments, the rotation or shifting can be by more than one but fewer than four positions, for example by rotating by two, three, or some other number of positions.

It is noted that, in some instances, a user may be required to set parameter setting options for a number of parameters that exceeds the number of parameters that can be displayed within a given parameter selection region, such as regions 502-508. In such circumstances, the indicator associated with that region may have a different appearance to indicate to a user that such additional, non-displayed parameters are required to be selected. In the example embodiment shown, indicator 526 has a different and highlighted appearance that is visually distinct from both indicator 524 and from the display within parameter selection region 504 itself. For example, indicator 526 may have a brighter or different colored appearance as compared to indicator 524, which may have a general color and appearance that is consistent with, or closer to, the coloring and appearance of the modifier screen 500 overall. In this instance, indicator 526 identifies that there are additional parameters that are not within the default subset of parameters, but are within a total set of parameters associated with the SpO2 modifier, which are required to be selected.

Similar to rotation of the parameters, within a parameter setting option region there may be more parameter setting options than there are available parameter setting option subregions. In the example shown, parameter setting option regions 514, 522 each include an indicator 528, which identifies that additional parameter setting options are available beyond those shown in parameter setting option subregions. By way of contrast, parameter setting option region 520 includes four parameter setting option subregions and lacks an indicator, which identifies to a user that no additional parameter setting options are available beyond the four parameter setting options that are shown. Selection of indicator 528 will result in rotation of parameter setting options within the parameter setting option subregions; examples of manner of rotation are described in further detail below in connection with FIGS. 6-9.

It is noted that, in any of the types of rotation of parameters or parameter setting options described above, in example embodiments there may be a maximum of four or eight parameters to be displayed in each parameter selection region, with either two parameter setting option regions (in case there is a set of discrete options, such as position and location in region 502) or four parameter setting option regions (in case numerical inputs are required, such as flow rate and concentration within region 504). Likewise, there are, in such embodiments, up to eight parameter setting options to be displayed in parameter setting option regions, with a maximum of four parameter setting option subregions available for display of such options at one time. As such, there are only a limited number of selections of an indicator that may be required to reach, or cycle through, all of the parameters or options that are available. It is recognized that this use of four or eight regions is selected to ensure visibility and readability of the parameters and options on a screen of a typical medical device 105 as described above; however, when using larger or smaller screen types, other numbers of parameters may be selected for display at one time, for example based on the size of the screen, the user's expected distance from the screen, and the number of parameters and/or options to be displayed.

Various methods of rotating the display of parameter setting options that are also applicable to rotating display of parameters themselves are provided below in connection with FIGS. 6-9. Furthermore, to minimize a number of selections of an indicator that may be required, the parameters and parameter options may be organized to include a default set of parameters and parameter setting options in an initial display that are most likely to be selected, with parameters and/or parameter setting options not displayed being less likely to be selected.

Referring to FIG. 5 generally, it is noted that because each of the parameter selection regions and parameter setting option subregions have a predetermined size (e.g., width), a predetermined number of parameters can be displayed at a single time. In the context of the modifier screen 500, in some embodiments in which space is needed to be conserved, a single indicator may be presented in association with a given region, rather than allowing for two indicators and bidirectional rotation of the parameters and/or parameter setting options. This allows for conservation of space that is reserved for display of parameters and options associated with each modifier.

In the embodiment shown, additional confirmation selection buttons are included, such as the "Next" button 530 and a "Cancel" button 532. User selection of the "Next" button 530 will cause the medical device to assess whether all of the parameters that are required to be set have associated selected parameter selection options. For example, the medical device will not only determine that parameters are set for the default set of modifiers presented on the modifier screen 500 initially, but also any parameters that are to be displayed in response to indicator 526 which identifies that additional parameters that are not initially displayed require selection. If not all parameters have been selection, a notification screen may be presented to the user, indicating to set all relevant parameters. If all parameters have been selected, the display may proceed to either an additional screen or return to the home screen 400, as noted above in connection with FIG. 3. Additionally, if the "Cancel" button 532 is selected, the display may return to the home screen 400, as identified in FIG. 3.

It is noted that although referred to herein as regions and/or subregions of a screen, such regions or subregions may have a particular appearance. For example, in the example shown, the subregions appear as selectable buttons that are included in a contiguous line of buttons included in a region and including (in some cases) an indicator button used to view additional options; in alternative embodiments, different sized/shaped buttons could be used, or different styles of selection mechanisms could be used as well, consistent with the present disclosure.

Referring now to FIGS. 6-9, various rotational mechanisms for navigating a sequence of parameter options for a given parameter are shown. The parameter option navigation sequence is shown as applicable to a parameter setting option region and rotation of parameter options through parameter setting option subregions, for example using indicator 528 of the modifier screen 500; however, it is equally applicable to rotation of parameters and parameter setting option regions within a parameter selection region, as identified above, for example using indicators 524, 526 of the modifier screen 500.

For purposes of illustration of the methods of rotation in FIGS. 6-9, a set of six parameter options, identified for simplicity as parameter options One, Two, Three, Four, Five, and Six are included for a particular parameter, and available to be selected. When a desired parameter option is displayed in a visible parameter option subregion, a user may select that parameter option by selecting that corresponding parameter selection option subregion, thereby setting that option for the associated parameter. It is noted that up to eight parameter options can be included for each parameter that uses such preset options; similarly, up to four different parameters having parameter options can be set in each parameter selection region of FIG. 5.

Figure 6:
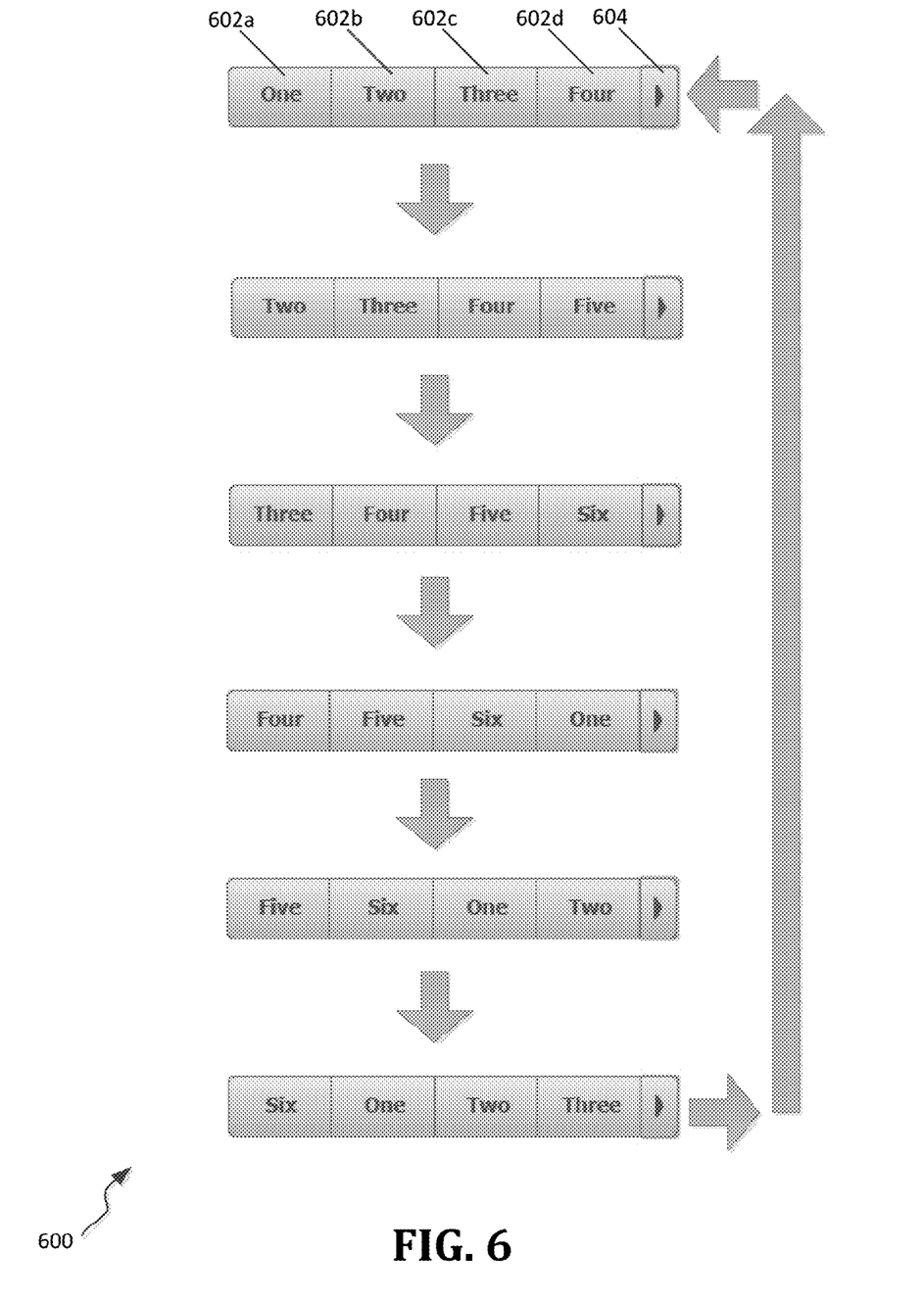
FIG. 6 illustrates a navigation sequence for selecting a parameter option using a set of parameter setting option subregions and an indicator, according to a first possible embodiment.

Referring first to FIG. 6, a navigation sequence 600 is shown in which a parameter setting option region includes four parameter setting option subregions 602a-d and an indicator 604. In a default, or initial, state, four parameter options, identified as One, Two, Three, and Four, are displayed. After a first selection of indicator 604, the parameter options are rotated one position to the left, causing parameter option One to no longer be displayed, parameter options Two, Three, and Four to rotate one parameter setting option subregion to the left, and a previously-undisplayed parameter option, i.e., option Five, to be displayed at an opposite side of the parameter setting option region from the side from which parameter option One rotated off of the display. Similarly, after a second selection of indicator 604, parameter option Two disappears, parameter options Three, Four, and Five rotate one subregion to the right, and parameter option Six is newly displayed adjacent the indicator and at a position opposite the side where parameter option two disappeared. After a third selection of the indicator, parameter option Three disappears, with parameter options Four, Five, and Six rotating to the left one subregion and parameter option One reappearing. Similar sequences occur after subsequence selection of the indicator 604, thereby allowing for cycling of the parameter options, one position at a time, through the parameter selection option subregions.

Figure 7:
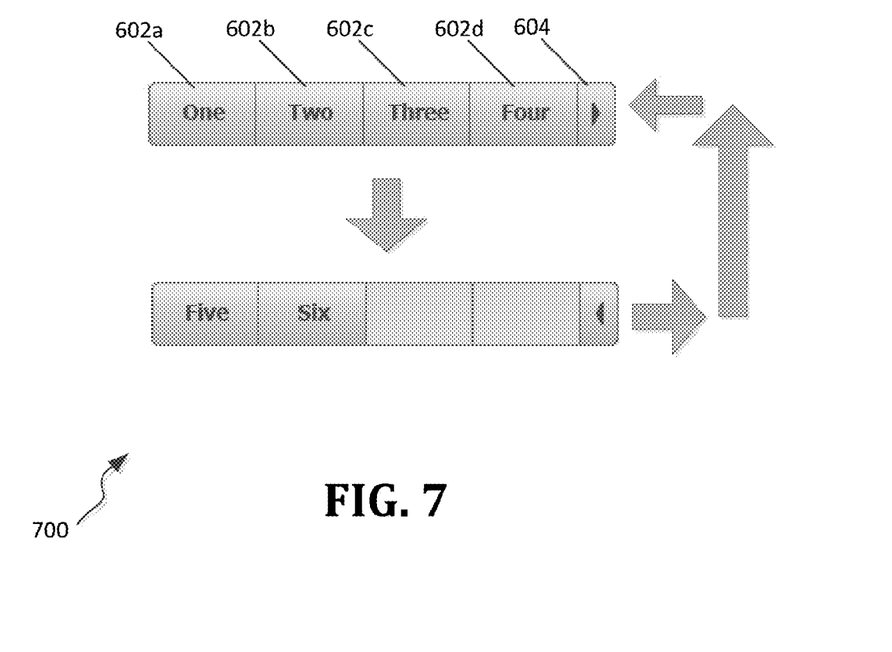
FIG. 7 illustrates a navigation sequence for selecting a parameter option using a set of parameter setting option subregions and an indicator, according to a second possible embodiment.

Referring now to FIG. 7, an alternative navigation sequence 700 is shown. In navigation sequence, the four parameter setting option subregions 602a-d and indicator 604 are initially displayed, analogous to the initial display in FIG. 6. In this embodiment, after a single selection of the indicator, the parameter options are rotated by four positions at a time, or completely "paged" on/off the display. Accordingly, after selection of the indicator once, parameter options Five and Six are displayed, rather than options One through Four. Furthermore, because there are fewer than eight available parameter options, two "placeholder" parameter options are provided, rather than rotating in display of parameter options One and Two in the rightmost two parameter setting option subregions 602c-d. In this embodiment, when no parameter options are displayed in a parameter setting option subregion (e.g., in the case of parameter setting option subregions 602c-d after selection of the indicator), those parameter setting option subregion(s) have a visual appearance that is generally flat or otherwise indicative that selection of those subregion(s) will have no effect. In other words, active subregions available for selection will appear as selectable "buttons" on the display, while subregions lacking such options may not appear to be buttons that are selectable.

Figure 8:
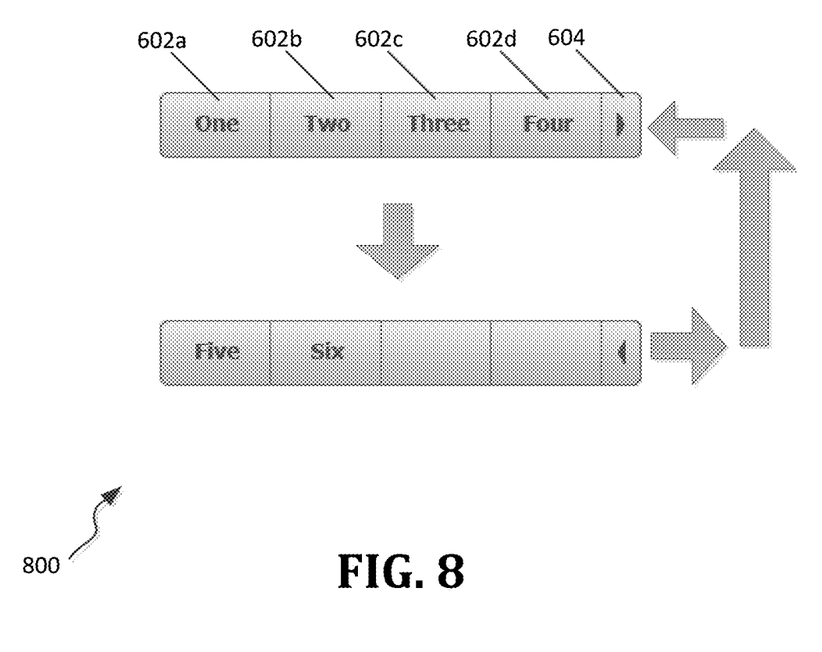
FIG. 8 illustrates a navigation sequence for selecting a parameter option using a set of parameter setting option subregions and an indicator, according to a third possible embodiment.

Similarly, navigation sequence 800 of FIG. 8 is generally analogous to that shown in FIG. 7, but in the case of parameter setting option subregion(s) that lack display of a parameter option, the parameter setting option subregions will maintain a uniform appearance compared to the remaining, "active" parameter setting option subregions. Accordingly, after a first selection of indicator 604 within navigational sequence 800, parameter setting option subregions 602a-b and 602c-d have similar appearance, despite parameter setting option subregions 602c-d lacking associated parameter options displayed therein. As such, each of parameter setting option subregions 602a-d appear to be selectable "buttons" despite parameter setting option subregions 602c-d lacking an associated parameter option that can be selected.

Figure 9:
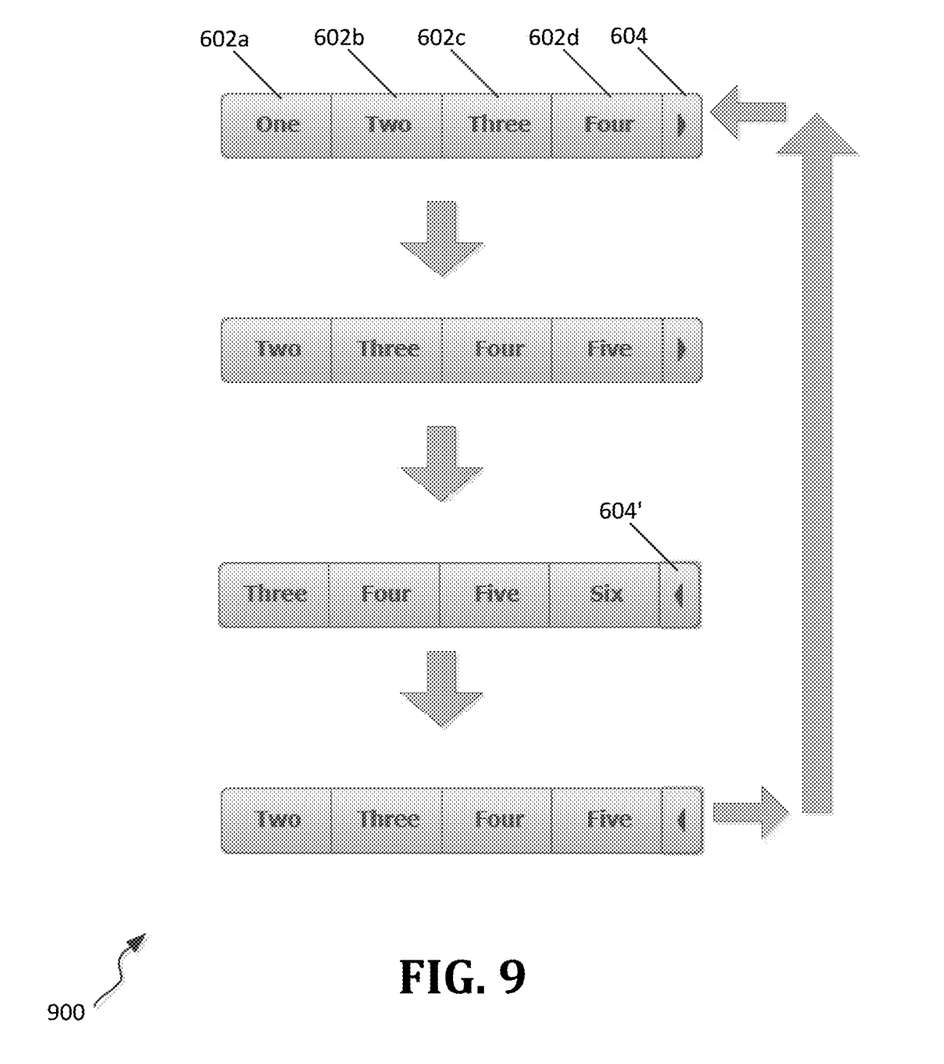
FIG. 9 illustrates a navigation sequence for selecting a parameter option using a set of parameter setting option subregions and an indicator, according to a fourth possible embodiment.

Referring to FIG. 9, a still further example of a navigation sequence for display of parameter options within parameter setting option subregions is shown. In this example, the indicator will provide for bidirectional rotation rather than the "wrap-around" functionality shown in FIG. 6. In particular, a first selection of indicator 604 will have similar functionality to that seen in FIG. 6; however, second and subsequent selections will cause different behavior. In particular, a second selection of the indicator 604 will reach the last of the parameter options ("Six"), and therefore will cause the indicator 604 to have an updated visual appearance, shown as 604'. Indicator 604' displays an arrow in an opposite direction, indicating that subsequent selection of that indicator will cause rotation of the parameter options to the left, rather than to the right. Accordingly, a third selection of the indicator 604' will cause display of options Two, Three, Four, and Five (hiding option Six). Similarly, a fourth selection of indicator 604' will cause display of options One, Two, Three, and Four (hiding option Five). The fourth selection of indicator 604' will also cause return of the indicator to display showing rotation to the right, because option One is a first option in the sequence.

It is noted that additional methods of rotating a display of parameters and parameter options may be possible as well within the scope of the present disclosure. For example, rotation by two or more positions, but not by all four positions, may be desirable. Furthermore, more or fewer parameter setting option regions for each modifier and/or parameter setting option subregions for each parameter may be included in a display. Furthermore, although a total set of eight parameter options is described herein as a method of limiting the number of indicator selections that would be required, it is noted that in some embodiments additional parameter options could be included as well, consistent with the scope of the present disclosure. It is noted that each such embodiment may have advantages over existing solutions involving complex drop-down menus and other types of selection sequences in which a relatively larger number of user actions is required to select a particular parameter and an appropriate, associated parameter option. Furthermore, it is again noted that although the example display navigation sequences of FIGS. 6-8 are described in the context of parameter setting option subregions, analogous navigation could be provided for cycling through parameter setting option regions within a parameter selection region, or other types of region selection configurations.

Figure 10:
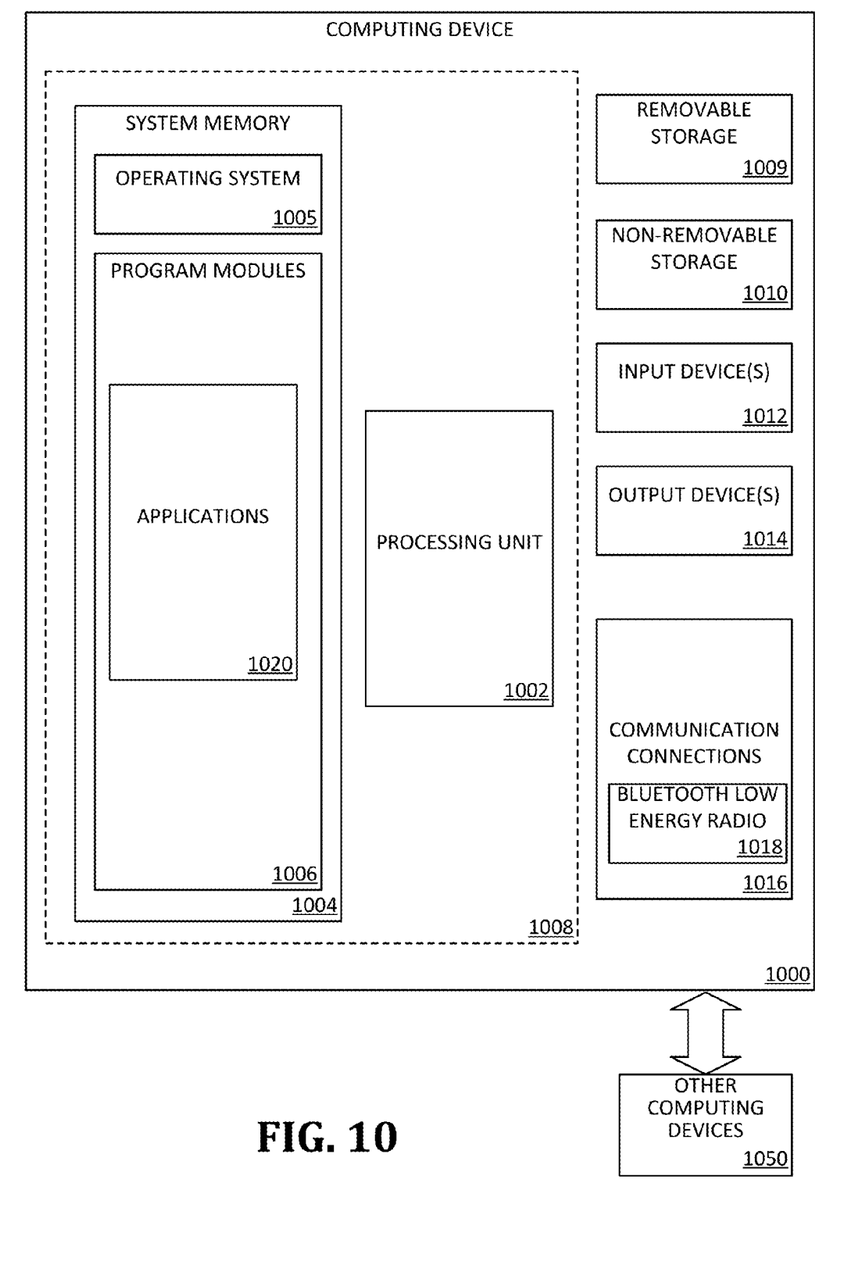
FIG. 10 is a block diagram illustrating physical components of a computing device with which examples and embodiments of the disclosure can be practiced.

FIG. 10 is a block diagram illustrating physical components (i.e., hardware) of a computing device 1000 with which embodiments of the disclosure may be practiced. The computing device components described below may be suitable to act as the computing devices described above, such as wireless computing device and/or medical device of FIG. 1. In a basic configuration, the computing device 1000 may include at least one processing unit 1002 and a system memory 1004. Depending on the configuration and type of computing device, the system memory 1004 may comprise, but is not limited to, volatile storage (e.g., random access memory), non-volatile storage (e.g., read-only memory), flash memory, or any combination of such memories. The system memory 1004 may include an operating system 1005 and one or more program modules 1006 suitable for running software applications 1020. The operating system 1005, for example, may be suitable for controlling the operation of the computing device 1000. Furthermore, embodiments of the disclosure may be practiced in conjunction with a graphics library, other operating systems, or any other application program and is not limited to any particular application or system. This basic configuration is illustrated in FIG. 6 by those components within a dashed line 1008. The computing device 1000 may have additional features or functionality. For example, the computing device 1000 may also include additional data storage devices (removable and/or non-removable) such as, for example, magnetic disks, optical disks, or tape. Such additional storage is illustrated in FIG. 10 by a removable storage device 1009 and a non-removable storage device 1010.

Other program modules that may be used in accordance with embodiments of the present disclosure, and in particular to generate screen content, may include electronic mail and contacts applications, word processing applications, spreadsheet applications, database applications, slide presentation applications, drawing or computer-aided application programs, etc.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 6 may be integrated onto a single integrated circuit. Such an SOC device may include one or more processing units, graphics units, communications units, system virtualization units and various application functionality all of which are integrated (or "burned") onto the chip substrate as a single integrated circuit. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

The computing device 1000 may also have one or more input device(s) 1012 such as a keyboard, a mouse, a pen, a sound or voice input device, a touch or swipe input device, etc. The output device(s) 1014 such as a display, speakers, a printer, etc. may also be included. The aforementioned devices are examples and others may be used. The computing device 1000 may include one or more communication connections 1016 allowing communications with other computing devices 1018. Examples of suitable communication connections 1016 include, but are not limited to, RF transmitter, receiver, and/or transceiver circuitry; universal serial bus (USB), parallel, and/or serial ports. Additionally, the communication connections 1016 can include a Bluetooth Low Energy Radio.

The term computer readable media as used herein may include non-transitory computer storage media. Computer storage media may include volatile and nonvolatile, removable and non-removable media implemented in any method or technology for storage of information, such as computer readable instructions, data structures, or program modules. The system memory 1004, the removable storage device 1009, and the non-removable storage device 1010 are all computer storage media examples (i.e., memory storage.) Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 1000. Any such computer storage media may be part of the computing device 1000. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Embodiments of the present disclosure may be utilized in various distributed computing environments where tasks are performed by remote processing devices that are linked through a communications network in a distributed computing environment.

The logical flows depicted herein are just examples. There may be many variations to these diagrams or the steps (or operations) described therein without departing from the spirit of the disclosure. For instance, the steps may be performed in a differing order, or steps may be added, deleted or modified.

While embodiments have been described, it will be understood that those skilled in the art, both now and in the future, may make various improvements and enhancements can be made.

The invention claimed is:

1. A medical device comprising:
   a processor;
   a display;
   a memory having encoded instructions stored thereon that, when executed by the processor, cause the processor to create a patient monitoring interface on the display, the patient monitoring interface including:
   a home screen displaying a plurality of monitored values in a corresponding plurality of home screen monitoring regions, and wherein one or more of the home screen monitoring regions includes a modifier display subregion displaying one or more selected modifiers including parameters and selected parameter options selected in the modifier screen;
   a modifier screen reached based on selection of the modifier display subregion and including a plurality of parameter selection regions, each of the plurality of parameter selection regions included in a row aligned with a modifier of a patient measurement to be monitored and having a predetermined number of subregions associated with different parameters, and wherein the predetermined number of subregions is lower than a total number of parameters associated with the modifier;
   wherein the modifier screen further includes:
   for at least one of the plurality of parameter selection regions, display of an initial parameter in each of the plurality of parameter selection subregions and display of a first indicator region at an end of the row which, when selected, causes the plurality of parameter selection subregions to cycle through a set of parameters, the set of parameters including a number of parameters greater than the number of parameter selection subregions; and for at least one of the plurality of parameter selection subregions, display of a plurality of parameter setting option subregions and a second indicator region, which, when selected, causes the plurality of parameter setting option subregions to cycle through a set of parameter settings, the set of parameter settings including a number of parameter settings greater than the number of parameter setting option subregions;

wherein the second indicator region includes an arrow positioned in a first direction to allow the plurality of parameter setting option subregions to cycle through the set of parameter settings in a first direction until an end is reached; and wherein, when the end is reached, the arrow changes direction to allow the plurality of parameter setting option subregions to cycle through the set of parameter settings in an opposite second direction wherein, the processor is further configured to, in response to selection by a user of a confirmation button on the modifier screen, determine whether a required parameter setting option remains unselected, and, in response to determining that a required parameter setting option remains unselected, display a notification message on the display indicating to select the required parameter setting option.

* * * * *